United States Patent [19]

Porot

[11] Patent Number: 5,817,919

[45] Date of Patent: Oct. 6, 1998

[54] LEAK RATE CONTROL PROCESS AND APPLICATION OF THE PROCESS TO THE MEASUREMENT OF THE PROPORTION OF GAS IN A LIQUID

[75] Inventor: Pierre Porot, Paris, France

[73] Assignee: Institut Francais du Petrole, Rueil-Malmaison, France

[21] Appl. No.: 676,920

[22] Filed: Jul. 8, 1996

[30]     Foreign Application Priority Data

Jul. 11, 1995 [FR]  France ................................. 95 08493

[51] Int. Cl.⁶ ............................................... G01N 7/00
[52] U.S. Cl. ............................................................ 73/19.1
[58] Field of Search ........................ 73/19.05, 19.06, 73/19.1, 19.01

[56]          References Cited

FOREIGN PATENT DOCUMENTS 0 349 374   1/1990   European Pat. Off. .
0 521 753   1/1993   European Pat. Off. .
2 670 894   6/1992   France .
25 14 625  10/1975   Germany .

*Primary Examiner*—Michael Brock
*Attorney, Agent, or Firm*—Antonelli, Terry, Stout & Kraus, LLP

[57]              ABSTRACT

The present invention is a process for controlling a leak rate in a measuring system comprising an element under pressure, by allowing a leak rate proportional to the pressure from the system and in varying the leak rate in the manner as the pressure charge. The present invention allows lower high pressure to be applied to the element under pressure in order to obtain a given proportion of gas and therefore to reach the proportion of gas more rapidly by applying lower pressures to the element under pressure.

1 Claim, 2 Drawing Sheets

LEAK RATE CONTROL PROCESS AND APPLICATION OF THE PROCESS TO THE MEASUREMENT OF THE PROPORTION OF GAS IN A LIQUID

BACKGROUND OF THE INVENTION

1. Field of the Invention

The present invention relates to the field of measurements comprising an element under pressure.

More precisely, the present invention relates to the control of a leak rate in a system comprising an element placed under pressure.

The present invention particularly pertains to processes for allowing determination of a proportion of gas present in a liquid, as disclosed for example in French patent FR-2,670,894.

2. Description of the Prior Art

A known process notably consisting of confining a sample of a gas-liquid mixture in a chamber, compressing the mixture and measuring the relative volume variation as well as the pressure variation in the chamber.

This type of process allows for example the determination of the proportion of air in oil fed to an internal-combustion engine.

According to French patent FR-2,670,894, a low, minimum leak rate is sought because it appeared that leaks disturb measurements of relative volume separation and pressure variation in the chamber. It was therefore tried, in this prior art, to prevent the gas from leaking out.

SUMMARY OF THE INVENTION

It has been unexpectedly discovered that the leak rate does not necessarily have a negative effect on these measurements.

In particular, it has been observed that a low leak rate is negligible when the pressure itself is low. Besides, a higher leak rate, associated with a pressure that is also higher, has no negative effect on the measuring result, as explained hereafter.

These objects and advantages are reached according to the invention which relates to a process for controlling a leak rate in a measuring system comprising an element under pressure.

According to the invention, the control process allows a leak rate substantially proportional to the pressure of the element under pressure and in varying the leak rate in the same way as the pressure.

A preferred application of the invention relates to the determination of the proportion of gas present in a liquid. According to this application, the process applies high pressures to the element under pressure in order to obtain a given proportion of gas.

Furthermore, the invention determines more rapidly the proportion of gas by applying to the element under pressure lower pressures in relation to the prior art.

BRIEF DESCRIPTION OF THE DRAWINGS

Other features, details and advantages of the present invention will be clear from reading the description hereafter, given by way of non limitative examples, with reference to the accompanying drawings in which.

DESCRIPTION OF THE PREFERRED EMBODIMENTS

Figure 1:
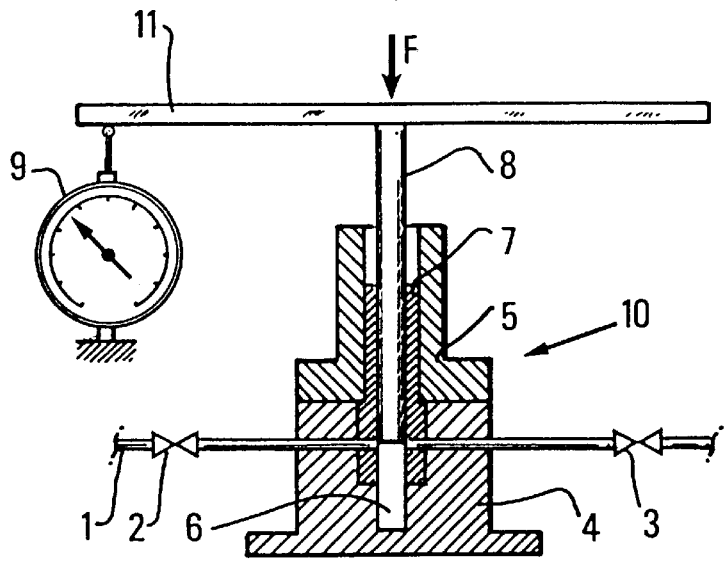
FIG. 1 diagrammatically shows a measuring assembly for measuring the proportion of gas in a liquid, according to the prior art.

FIG. 1 shows a longitudinal section of a device 10 by means of which volume and pressure measurements can be carried out. A pipe 1 allows the mixture to flow into device 10. Two valves 2, 3, one upstream, the other downstream from the device, are intended to isolate device 10 from the rest of the pipe. The device includes a casing that may be made up of two parts 4, 5, and which comprises an indeformable cylindrical mixture-receiving cavity 6. A seal element 7 surrounds a piston 8 intended to compress the mixture. Delivery pipe 1 runs right through the lower casing 4 and opens into the upper part of cavity 6. Piston 8, coaxial to cavity 6, can isolate the latter with respect to delivery pipe 1 by sealing the upper part thereof.

Any additonal means can also be provided in order to isolate cavity 6 from delivery pipe 1 by sealing the upper part thereof.

An axial displacement of piston 8 allows the mixture to be compressed within cavity 6. This displacement is measured by any means known in the art, such as displacement pickup 9 in FIG. 1. A horizontal element 11 in contact with piston 8 and a displacement pickup 9 allows the location of the level of piston 8 to be determined and therefore transmits any displacement of the piston to pickup 9.

Figure 2:
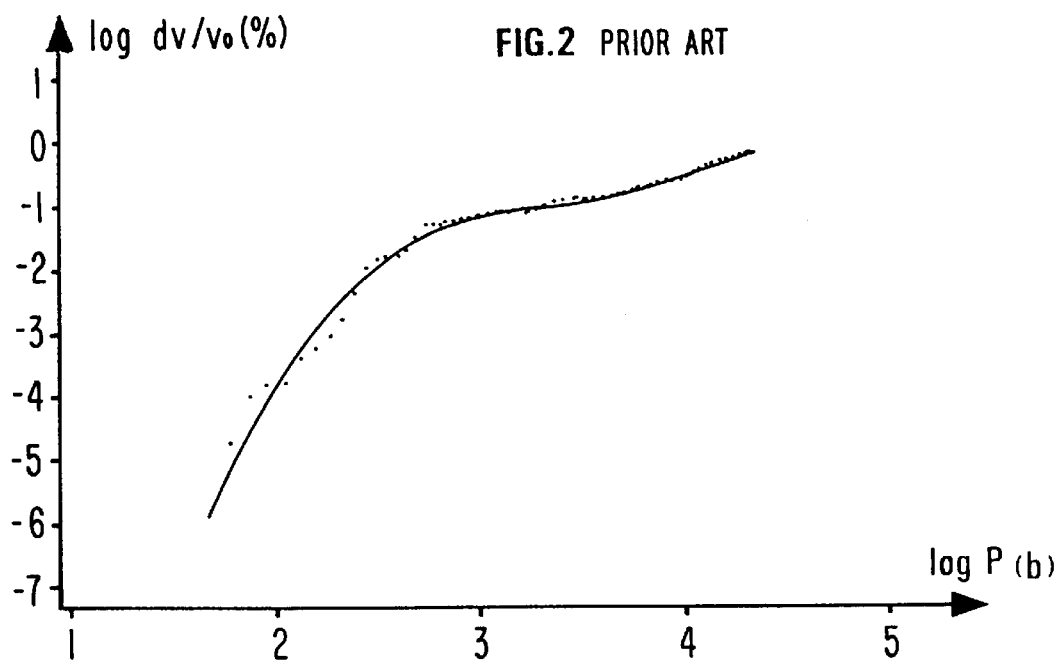
FIG. 2 is a curve obtained according to the prior art, defined by the logarithm of the relative variation of the volume sampled as a function of the logarithm of the pressure applied to the sample.

The experimental curve obtained in FIG. 2 gives the relative volume compression of the sample as a function of the relative pressure applied to the sample. This curve exhibits an inflexion point whose ordinate corresponds to the proportion of gas present in the liquid sampled.

According to this curve given by way of example, the inflexion point appears for a log P substantially greater than 3, which corresponds to real pressures of the order of 1000 bars on the sample. It sometimes takes a long time to obtain these pressures, especially when a slow pressure buildup is required. Besides, the sample does not always withstand such pressures: it may degrade, decompose . . . before the inflexion point appears.

Advantageously, this limitation does not exist when the invention is implemented.

In fact, the present invention allows the inflexion point to be shifted on the abscissa but not on the ordinate. In other words, the value that is sought, here the proportion of gas in the liquid, remains unchanged in relation to the prior art.

On the other hand, the pressure to be applied is reduced by a factor that may amount to up to 10.

Figure 3:
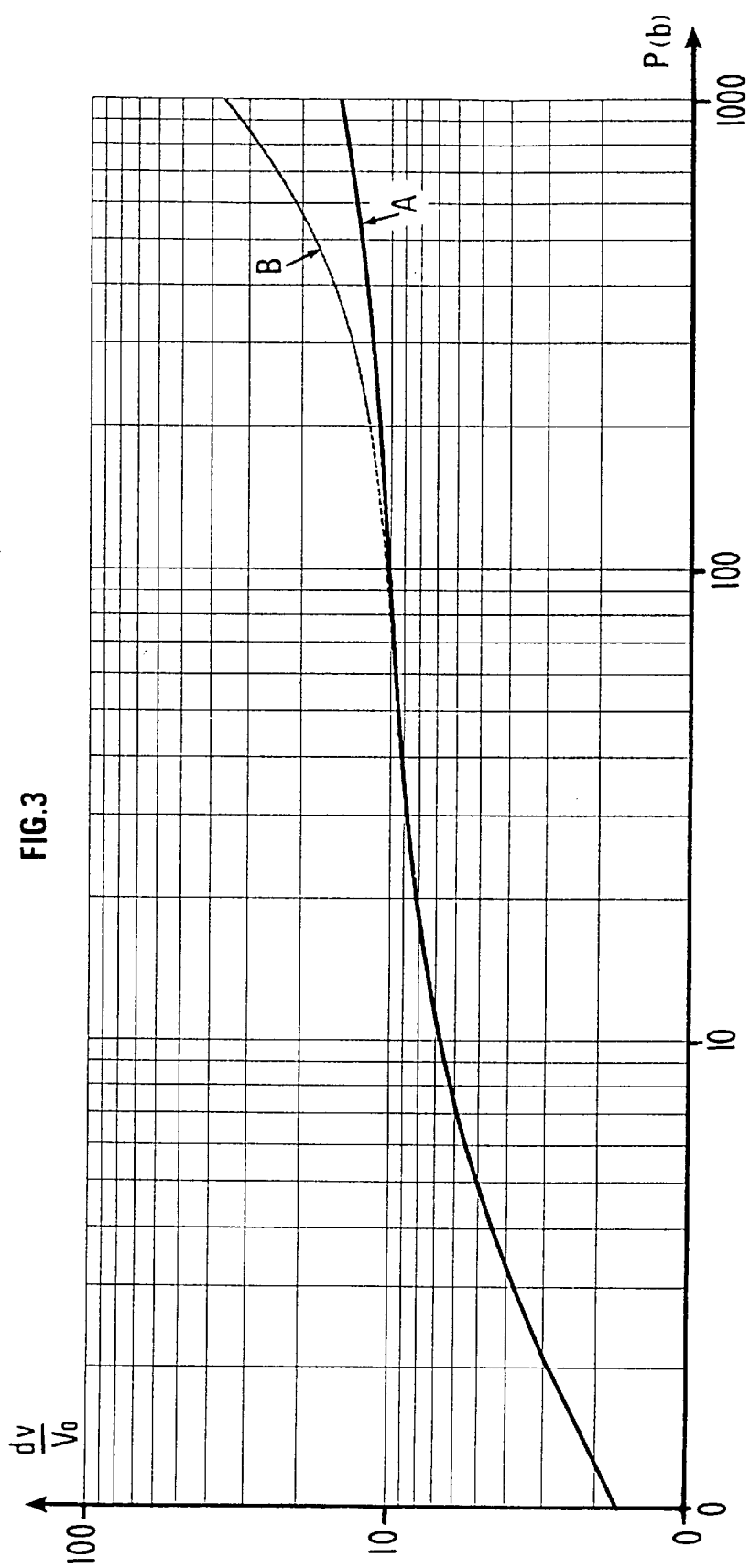
FIG. 3 shows two curves, one (B) obtained according to the invention and the other (A) according to the prior art, both defined by the same parameters as the curve in FIG. 2.

FIG. 3 illustrates this difference well. It relates to the measurement of the proportion of air in oil. A curve A (full line) according to the prior art and a curve B (dotted line) according to the invention can be seen in this figure, both varying around an inflexion point. These curves vary differently above a certain relative pressure of the sample; curve A does not vary much on the ordinate, it remains flat for a very long time, thus leaving a longer uncertainty on the inflexion point.

Curve B obtained by establishing and by controlling a leak rate according to the invention, exhibits an inflexion point from a 200-bar relative pressure. Under the same conditions, at least a 500-bar relative pressure has to be reached according to the prior art to allow an inflexion point to be determined.

Advantageously, many measurements showed that the inflexion point is not shifted on the ordinate.

According to the invention, a leak rate proportional to the pressure thus has to be established at the level of the element placed under pressure: a negligible low leak rate is established when the pressure is low and a higher leak rate is generated when the pressure is higher.

According to the preferred application of the invention illustrated in FIG. 3, a low leak rate is generated in the first part of the curve, i.e. for pressures of several ten bars. Besides, a higher leak rate is established when the inflexion point of the curve is approached, i.e. on the flattest part of the curve.

In relation to the prior art, the present invention thus allows location of lowered high pressures to the element under pressure in order to obtain a given proportion of gas.

Thus, according to the invention, the proportion of gas is obtained more rapidly by applying lower pressures to the element under pressure.

According to a first theoretical approximation, we may in fact write that the leak rate ($Q_F$) is proportional to the pressure (P) of the sample: $Q_F = K.P$.

With reference to the curve of FIG. 3, the leak rate ($Q_F$) must be less than the oil compressibility rate D below the inflexion point, and this same rate has to be higher than the oil compressibility rate above the inflexion point.

We know that $$D = \frac{V_o}{B} \times \frac{dP}{dt}$$

where $V_o$ = sample initial volume

B = oil compressibility modulus (application case of FIG. 3) ~ $15 \times 10^8$ Pa $$\frac{dP}{dt} = \text{compression velocity} \approx 1 \text{ bar}/s.$$

Around 100 bars, the leak is equivalent to the compressibility rate.

$$Q_F = KP = \frac{V_o}{B} \times \frac{dP}{dt} \rightarrow K = \frac{V_o}{B.P} \times \frac{dP}{dt}$$

$$\text{Let: } K = \frac{10^5 \times V_o}{15 \times 10^8 \times 10^7} = 6.6 \times 10^{-12} \times V_o$$

Below the inflexion point, i.e. for pressures on the sample less than 100 bars, of the order of 10 bars for example:

$Q_F < KP$ $Q_F < 6.6 \times 10^{-12} V_o 10^6$ $Q_F < 6.6 \times 10^{-6} \times V_o$.

For pressures of the order of 100 bars and more:

$Q_F > 6.6 \times 10^{-12} \times V_o \times 10^7$ $Q_F > 6.6 \times 10^{-5} = V_o$.

The values mentioned above are given by way of non limitative example for determining the proportion of air in oil.

The present invention provides a real improvement of this measuring range and it can of course be generalized to any measurements comprising an element placed under pressure, under the above-mentioned conditions.

I claim:

1. A process for measuring a proportion of gas present in a liquid comprising:

placing the liquid containing the gas in a chamber;

applying increasing pressure to the liquid and gas within the chamber while controlling a set rate of leakage of the liquid and gas from the chamber with the proportion of gas during the applying of increased pressure being determined from an inflection point, in which compressibility is represented along an ordinate and pressure is represented along an abscissa, which is a flattest part of variation along the ordinate and the rate of leakage is controlled so that the set rate of leakage is increased as the pressure is increased.

* * * * *